United States Patent
Gorenstein et al.

(10) Patent No.: US 6,423,493 B1
(45) Date of Patent: Jul. 23, 2002

(54) COMBINATORIAL SELECTION OF OLIGONUCLEOTIDE APTAMERS

(75) Inventors: David G. Gorenstein, Houston; David J. King, Galveston; Daniel A. Ventura, Galveston; Allan R. Brasier, Galveston, all of TX (US)

(73) Assignee: Board of Regents the University of Texas System, Austin, TX (US)

( * ) Notice: Subject to any disclaimer, the term of this patent is extended or adjusted under 35 U.S.C. 154(b) by 0 days.

(21) Appl. No.: 09/425,798

(22) Filed: Oct. 25, 1999

Related U.S. Application Data (60) Provisional application No. 60/105,600, filed on Oct. 26, 1998.

(51) Int. Cl.⁷ .............................. C12Q 1/68; C12P 19/34
(52) U.S. Cl. ........................ 435/6; 435/91.2; 435/7.1; 435/DIG. 47
(58) Field of Search ..................... 536/23.1; 514/44; 435/6, 91.2, 7.1, DIG. 47

(56) References Cited

U.S. PATENT DOCUMENTS

| | | | |
|---|---|---|---|
| 5,218,088 A | 6/1993 | Gorenstein et al. | 536/25.34 |
| 5,397,698 A | 3/1995 | Goodman et al. | 435/6 |
| 5,475,096 A | * 12/1995 | Gold et al. | 536/23.1 |
| 5,576,302 A | 11/1996 | Cook et al. | 514/44 |
| 5,587,361 A | * 12/1996 | Cook et al. | 514/44 |
| 5,599,797 A | 2/1997 | Cook et al. | 514/44 |
| 5,602,000 A | 2/1997 | Hyman | 435/91.1 |
| 5,607,923 A | 3/1997 | Cook et al. | 514/44 |
| 5,620,963 A | 4/1997 | Cook et al. | 514/44 |
| 5,635,488 A | 6/1997 | Cook et al. | 514/44 |
| 5,639,873 A | 6/1997 | Barascut et al. | 536/25.3 |
| 5,661,134 A | 8/1997 | Cook et al. | 514/44 |
| 5,705,337 A | 1/1998 | Gold et al. | 435/6 |
| 5,734,041 A | 3/1998 | Just et al. | 536/25.31 |
| 5,763,595 A | 6/1998 | Gold et al. | 436/22.1 |
| 5,804,445 A | 9/1998 | Brasier | 435/375 |
| 5,874,219 A | 2/1999 | Rava et al. | 435/6 |

OTHER PUBLICATIONS

Ueda et al. (1991) Nucleic Acids Research 19(3):547–552.*

* cited by examiner

*Primary Examiner*—Padmashri Ponnaluri
*Assistant Examiner*—Thomas Friend
(74) *Attorney, Agent, or Firm*—Sanford E. Warren, Jr.; Edwin S. Flores; Gardere Wynne Sewell LLP (57) ABSTRACT

A random combinatorial selection method is disclosed for the construction of oligonucleotide aptamers in which nuclease resistance is conferred by the inclusion of modified nucleotides. The modified nucleotides are incorporated during PCR amplification to form achiral modified oligonucleotides. Thio-substituted aptamers are provided that bind tightly to the nuclear factor for human IL6 (NF-IL6).

21 Claims, 3 Drawing Sheets

COMBINATORIAL SELECTION OF OLIGONUCLEOTIDE APTAMERS

This application claims priority based on U.S. Provisional Application Ser. No. 60/105,600 filed Oct. 26, 1998.

This work was supported by the following United States Government grants DARPA (9624-107 FP) and NIH (AI27744).

TECHNICAL FIELD OF INVENTION

This invention relates generally to the generation of aptamers and to the use of aptamers as diagnostic and therapeutic agents. More particularly, the present invention relates to a method of using combinatorial chemistry to prepare novel oligonucleotide sequences having at least one thiophosphate replacement in the phosphate backbone and that have enhanced target binding properties.

BACKGROUND OF THE INVENTION

Without limiting the scope of the invention, its background is described in connection with oligonucleotide agents and with methods for the isolation and generation thereof.

Oligonucleotide agents have been shown to have functional activity in vitro and thus the promise of therapeutic potential. Some of these agents are believed to operate via mechanisms such as the sequence-specific antisense translation arrest of mRNA expression or through direct binding to protein targets where they function as "decoys". While oligonucleotide agents show therapeutic promise, various pharmacological problems must first be overcome.

Oligonucleotide agents have been used as high specificity therapeutic agents in vitro. High sensitivity to nuclease digestion, however, makes oligonucleotide agents unstable and thus impracticable for in vivo administration by either intravenous or oral routes.

From the foregoing it is apparent the there is a need in the art for methods for generating high binding, nuclease resistant oligonucleotide that retain their specificity. Also needed are compounds and methods that permit the generation of high binding, high specificity, nuclease resistant oligonucleotide agents that have an improved half-life and are target specific.

SUMMARY OF THE INVENTION

Aptamers may be defined as nucleic acid molecules that are selected from random or high-sequence diversity libraries due to their ability to bind with a target. An iterative process known as in vitro selection is used to enrich the library for species with high affinity to the target. The iterative process involves incubation of the library with the target, separation of target bound oligonucleotide ("TBO") sequences from free TBO and amplification of the bound and thus selected TBO population to enrich the library. Amplification may be effected enzymatically, for example, using a thermostable DNA polymerase in a polymerase chain reaction ("PCR"). The result is a sub-library populated with a small subset of sequences that have a high affinity for the target. The library is then subcloned to sample and preserve the target specific DNA, RNA or mixed sequences selected. These "lead compounds" may then be studied in further detail to elucidate the mechanisms by which they interact with the target.

The present invention is directed to the generation of aptamers that are nuclease resistant and therapeutically effective. In one embodiment of the present invention, a method is provided of selection of modified oligonucleotide aptamers wherein the modification of constituent nucleotides confers nuclease resistance to the oligomer. In a first step, a random single-stranded combinatorial library is chemically synthesized wherein the synthetic library includes at least one set of 5' and 3' primer segments flanking a randomized region. Next, the random combinatorial library is amplified and modified using enzymatic synthesis, for example, by PCR. The synthetic reaction is provided with a pool of four nucleotides including dA, dT, dG and dC, in which at least one, for example dA is used. Not all four nucleotides, however, are chemically modified prior to use in the reaction. The modified oligonucleotide library is then placed into contact with the target molecule. Nucleotides that bind the specific target are isolated from those which do not. Next, oligonucleotides binding to the target molecule are again amplified enzymatically in the presence of the desired modified nucleotide substrates. The isolation and amplification steps are repeated iteratively until at least one oligonucleotide population of defined sequence is obtained. Sequencing and cloning of target-selected aptamers is used to isolate, preserve and enhance the conformation of the aptamer.

In one embodiment of the present invention the nucleotide modification conferring nuclease resistance is thiolation of one or both of the non-bridging oxygens around the phosphorus. The present inventors have shown that various backbone modifications, such as the phosphorothioates and phosphorodithioates, may render aptamers more nuclease resistant while still permitting efficient uptake by cells (Wang, S., Lee, R. J., Cauchon, G. G., Gorenstein, D. G. & Low, P. S., *Proc. Natl. Acad. Sci., U.S.A.* (1995) 92: 3318).

Unfortunately, it has become apparent that oligonucleotides possessing high thiophosphate backbone substitutions appear to be "stickier" towards proteins than normal phosphate esters, attributable to non-specific interactions. (Cho, Y. S., Zhu, F. C., Luxon, B. A. & Gorenstein, D. G., J. Biomol. Struct. Dyn.(1993) 11: 685). Similarity, thiosubstitution may lead to structural perturbations in the structure of the duplex. Id. Even in specific protein-nucleic acid contacts, sulfurization of the internucleotide linkages leads to their enhanced binding (Milligan & Uhlenbeck, *Biochemistry* (1989) 28: 2849; Marshall & Caruthers, Science (1993) 259: 1564). As most of the direct contacts between DNA binding proteins and their binding sites are to the phosphate groups (Otwinowski et al., Nature (1988) 335: 321) the extent of incorporation of modified nucleotides must be controlled for thiosubstituted aptamers to retain target specificity. To this end, the present inventors have developed combinatorial library techniques where the phosphorothioate groups are controllably incorporated during library amplification rather than synthesized into "post library" selection oligonucleotide sequences. The method of the present invention provides optimization of the total number of thiophosphates incorporated into the aptamer. Thus, forming novel phosphorothioate oligonucleotides that are nuclease resistant yet have high specificity and high binding is achieved.

In another embodiment of the present invention, a method is provided for thiophosphate selection of nuclease resistant aptamers. In the first step, a random single-stranded combinatorial library is chemically synthesized where at least one set of 5' and 3' primer segments flanking a randomized region is included in the sequence. Next, the random combinatorial library is concurrently amplified and modified using enzymatic synthesis, e.g. PCR. The synthetic reaction is provided with a pool of four nucleotides including dA, dT, dG and dC, in which at least one is a thiophosphate.

Although a variety of methods may be employed for isolating aptamers, in one embodiment, target-oligonucleotide complexes are separated from non-binding oligonucleotides by filtration. Oligonucleotides binding to the target molecule are again amplified enzymatically in the presence of the desired thiophosphate nucleotide. The isolation and amplification may be repeated iteratively until at least one oligonucleotide population of defined sequences is obtained.

The method of the present invention was applied to NF-IL6 as a target. A specific binding sequence was obtained using the present invention to obtain a sequence that differs from the known consensus NF-IL6 binding domain. Thus, the present method provides for the generation of novel aptamers that are specific yet nuclease resistant. Although the present NF-IL6 aptamers were generated using monothiophosphate nucleotides, either mono or di-thiophosphate monomers may be used in a PCR reaction or by split synthesis ("mix and separate"), to incorporate these backbone modifications into the aptamer. Depending on whether monothiophosphate or dithiophosphate nucleotides are provided, similar or different sequences may be obtained thus expanding the repertoire of target specific aptamers to any given target.

In other aspects, the present invention is direct to the use of PCR to produce chiral duplex phosphothioaptamers using chiral monothiophosphate [$\alpha$S] nucleotide substrates. PCR amplification is conducted with an achiral or diastereomeric mixture of monothiophosphate [$\alpha$S] nucleotide substrates. When PCR is conducted using Taq polymerase, e.g., the polymerase selects among available thiophosphate nucleotides and, where an achiral mixture of thiophosphates is provided, the Taq polymerase incorporates only one enantiomer; thus producing a chiral duplex phosphorothioate oligonucleotide. Where for example, the nucleotides are a mix of DATP [$\alpha$S], dTTP, dGTP and dCTP, PCR amplication of the first single stranded library produces a chiral duplex phosphorothioate at all dA positions other than the primers.

The unique chemical diversity of the present library stems from both the nucleotide base sequence and phosphorothioate backbone sequence. Therefore, the present invention stems from the recognition that polymerases can incorporate chiral phosphorothioates and replicate a random sequence library simultaneously. Indeed this appears to be the first time any backbone modification of either RNA or DNA has been successfully carried out in this in vitro selection technology. The ability of PCR is exploited to amplify small quantities of DNA and enrich these populations for high affinity ligands. Unlike existing technology, however, phosphorothioate aptamers display increased nuclease resistance and are thus better suited for delivery to humans. Furthermore, simply replacing thiophosphates in a selected sequence for normal phosphate ester decreases (or increases) the affinity of the selected ligand for the target at random. Therefore, mere replacement of the ester backbone yields varying results invitro.

The method and identified sequences and compounds are also an improvement over existing antisense or "decoy" oligonucleotides because of their stereochemical purity. Chemically synthesized phosphorothioates are a diastereomeric mixture with $2^n$ stereoisomers with n being the number of nucleotides in the molecule. These preparations are unsuitable for use in humans because only a small fraction of the stereoisomers will have useful activity. Furthermore, the remaining could have potential adverse effects in vivo. In contrast, enzymatically synthesized oligonucleotides are stereochemically pure due to the chirality of polymerase active sites. Inversion of configuration is believed to proceed during incorporation of dNMP$\alpha$S into the DNA chain.

The present invention provides a method for producing oligonucleotide libraries where the phosphate backbone is substituted with phosphorothioate groups and wherein the substituted sites include at least a portion of the dA sites. The method also includes screening the library for binding to a target molecule or portion thereof that is highly selective, specific and with high affinity.

The present invention also provides oligonucleotide libraries of given or variable nucleotide sequence lengths where at least a portion of the phosphate backbone is substituted with phosphorothioate groups wherein a portion of the dA, dG, dC or dT phosphate sites are substituted with phosphorothioate groups. For example, substantially all of the dA, dG, dC or dT phosphate sites may be substituted with phosphorothioate groups.

The present invention also provides oligonucleotide libraries of given or variable nucleotide sequence lengths where at least a portion of the phosphate backbone is substituted with phosphorothioate groups. A portion of the phosphate sites in the library are substituted with phosphorothioate groups, e.g., where substantially all of phosphate sites are substituted with phosphorothioate groups. Particularly useful are aptamers where phosphate groups in the random nucleotide region of the oligonucleotide sequence library include one or more phosphorothioate backbone bonds.

The present invention contemplates and includes thioated aptamers with multiple substitutions. PCR amplification methods may be used to incorporate up to three dNTP$\alpha$S's into DNA. It is anticipated that dNTP$\alpha$S substitutions will provide the ability to further modulate the nuclease resistance of thioated aptamers and to provide greater diversity to the initial library.

Single-stranded nucleic acids are also known to exhibit unique structures. Single-stranded RNA and DNA may adopt unique structures. The present invention contemplates and includes the selection of single-stranded phosphorothioate aptamers (RNA and DNA). These compounds will find utility in the application of the present methodology and be used compounds that bind to otherwise non-DNA binding proteins (i.e., cell surface receptors, cytokines, etc.).

The present invention includes scaling-up technologies that necessarily follow from the development of methods for high throughput thio-aptamer selection. For example, 96 well microtiter plates may be used to select aptamers to a number of different proteins under varying conditions.

Based on the availability of sequencing using thiophosphate substitution (Nakamaye et al. *Nucl Acids Res.* (1988) 16: 9947), either backbone may be combinatorially selected and the substitutions identified at any position. The present invention contemplates and encompasses large-scale synthesis of defined stereochemistry and sequence thiophosphate aptamers using stereoregular monothiophosphate oligonucleotides (either R or S configuration at phosphorus for chemical synthesis). Using the present invention, random combinatorial libraries and selection for aptamers with a much greater diversity of structures ($7^n$ vs. $4^n$) are thus possible.

One embodiment of the present invention provides thioselected aptamers specific for the nuclear factor for IL-6

(NF-IL6). NF-IL6 is a basic leucine zipper transcriptional factor involved in the induction of acute-phase responsive and cytokine gene promoters in response IL-6 produces as a result of inflammation. Surprisingly, the thiophosphate selection method provided herein generated a NF-IL6 specific aptamer having a unique sequence different from that obtained using normal backbone selection methods.

Thiophosphate substituted oligonucleotides show reduced nuclease activity and enhanced interaction with proteins in general, not just DNA binding proteins. The present "thiophosphate-selection" method is applicable to the generation of novel aptamers selected against a wide array of targets that may be used therapeutically.

The present aptamers also find utility as biochemical research tools or medical diagnostics agents in cell culture, animal systems, in vitro systems and in the inhibition of high temperature polymerases (hot start PCR). The present invention may be used for the development of new anti-viral, anti-bacterial, anti-cancer, etc. agents. Under both physiological and in vitro conditions the present thioaptamers will provide tools to understand various pathological processes. The aptamers may also be used to develop compounds that have significant anti-pathological activity. Ultimately, they may be delivered as drugs to combat human disease.

BRIEF DESCRIPTION OF THE DRAWINGS

For a more complete understanding of the present invention, including features and advantages, reference is now made to the detailed description of the invention along with the accompanying figures.

DETAILED DESCRIPTION OF THE INVENTION

While the making and using of various embodiments of the present invention are discussed in detail below, it should be appreciated that the present invention provides many applicable inventive concepts which can be employed in a wide variety of specific contexts. The specific embodiment discussed herein are merely illustrative of specific ways to make and use the invention and do not delimit the scope of the invention.

ABBREVIATIONS

The following abbreviations are used throughout this application:
bZIP—basic leucine zipper
  BSA—bovine serum albumin
  CD—circular dichroism
  C/EBPβ—CCAAT-enhancer binding protein β
  DNase 1—Deoxyribonuclease 1
  DTT—dithiothreitol
    EDTA—ethylene diamine tetraacetic acid
    Il6—Interleukin-6
    kb—kilobase (pairs)
    kD—kilodalton
    $K_{obs}$—observed binding constant
    ODN—oligonucleotide
    NMR—nuclear magnetic resonance
    NF-KB—nuclear factor-kB
    NF-IL6—nuclear factor for human IL6
    dNTP($\alpha$S)—dNTP with monothiophosphorylation of the $\alpha$phosphate of the tripolyphosphate
    OD—optical density
    PAGE—polyacrylamide gel electrophoresis
    PCR—polymerase chain reaction
    RT—reverse transcriptase
    Taq—Thermus aquaticus DNA polymerase
    TCD—tryptic core domain of NF-IL6
    Tf—transcription factor To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, "synthesizing" of a random combinatorial library refers to chemical methods known in the art of generating a desired sequence of nucleotides, including random sequences. Typically in the art, such sequences are produced in automated DNA synthesizers programmed to the desired sequence. Such programming may include combinations of defined sequences and random nucleotides.

"Random combinatorial oligonucleotide library" means a large number of oligonucleotides of different sequence where the insertion of a given base at given place in the sequence is random.

"PCR primer nucleotide sequence" refers to a defined sequence of nucleotides forming an oligonucleotide that is used to anneal to a homologous or closely related sequence in order form the double strand required to initiate elongation using a polymerase enzyme.

"Amplifying" means duplicating a sequence one or more times. Relative to a library, amplifying refers to en masse duplication of at least a majority of individual members of the library.

As used herein, "thiophosphate" or "phosphorothioate" are used interchangeably to refer to analogs of DNA or RNA having sulphur in place of oxygen as one of the non-bridging ligands bound to the phosphorus. Monothiophosphates [$\alpha$S] have one sulfur and are thus chiral around the phosphorus center. Dithiophosphates are substituted at both oxygens and are thus achiral. Phosphorothioate nucleotides are commercially available or may be synthesized by several different methods known in the art.

"Modified" means oligonucleotides or libraries having oligonucleotides wherein one or more of the four constituent nucleotide bases are analogs or esters of nucleotides normally comprising DNA or RNA backbones and wherein such modification confers increased nuclease resistance. Thioated nucleotides are an example of modified nucleotides.

"Phosphodiester oligonucleotide" means a chemically normal (unmodified) RNA or DNA oligonucleotide.

Amplifying "enzymatically" refers to duplication of the oligonucleotide using a nucleotide polymerase enzyme such as DNA or RNA polymerase. Where amplification employs repetitive cycles of duplication such as using the "polymerase chain reaction", the polymerase is a heat stable polymerase such as the DNA polymerase of *Thermus aquaticus*.

"Contacting" in the context of target selection means incubating a oligonucleotide library with target molecules.

"Target molecule" means any molecule to which a specific aptamer selection is desired.

"Essentially homologous" means a sequence containing either the identified sequence or the identified sequence with one nucleotide substitution.

"Isolating" in the context of target selection means separation of oligonucleotide/target complexes, preferably DNA/protein complexes, under conditions in which weak binding oligonucleotides are eliminated. In one embodiment, the DNA/protein complexes are retained on a filter through which non-binding oligonucleotides are washed.

By "split synthesis" it is meant that each unique member of the combinatorial library is attached to a separate support bead on a two column DNA synthesizer, a different thiophosphoramidite is first added onto both identical supports (at the appropriate sequence position) on each column. After the normal cycle of oxidation and blocking (which introduces the dithiophosphate linkage at this position), the support beads are removed from the columns, mixed together and the mixture reintroduced into both columns. Synthesis may proceed with further iterations of mixing or with distinct nucleotide addition.

A recent advance in combinatorial chemistry has been the ability to construct and screen large random sequence nucleic acid libraries for affinity to proteins (Gold et al., *Proc. Natl. Acad. Sci. U.S.A.* (1997) 94: 59; Tian et al., *RNA* (1995) 1: 317; Ekland et al., *Science* (1995) 269: 364). The nucleic acid libraries are usually selected by incubating the target protein with the library and then employing a method of separating the non-binding species from the bound. The bound fractions are then amplified using PCR and subsequently incubated again with the protein for a second round of the screening or selection process. These iterations are repeated until the library is enhanced for sequences having high affinity for the target protein.

Agents selected from combinatorial libraries of RNA and DNA in the past have normal phosphate ester backbones and thus are generally unsuitable as drugs in vivo because of their nuclease susceptibility. Although varying degrees of nuclease resistance may be obtained using modified nucleotides, for example, by thiosubstitution at the non-binding oxygen groups of the phosphate backbone, the present inventors recognized that the functional effect of substitution of nuclease resistant thiophosphates could not be predicted since the sulfur substitution may lead to either decreased or increased binding to a specific protein.

The present inventors developed a novel combinatorial approach involving the construction and screening of a phosphorothioate DNA library. In one embodiment, the target selected was the nuclear factor for IL6 (NF-IL6), a basic leucine zipper transcription factor involved in the induction of acute-phase responsive and cytokine gene promoters in response to inflammation (Akira & Kishimoto, *Immun. Rev.* (1992) 127:25).

The following examples are include for the sake of completeness of disclosure and to illustrate the methods of making the compositions and composites of the present invention as well as to present certain characteristics of the compositions. In no way are these examples intended to limit the scope or teaching of this disclosure.

EXAMPLE 1

Thioselection of Phosphorodithioate Aptamers Binding to NF-IL6

The present invention provides oligonucleotide combinatorial methods that may be extended to selection not only of base sequence but of phosphate (or monothiophosphate) backbones as well. The best monothiophosphate aptamers were obtained using the following method. As an example, binding was increased at least 5-fold to the NF-IL6 tryptic core domain (TCD) than the normal backbone sequence. The sequences selected, while related to the normal backbone CAAC/T half-sites (for Family B below), show distinct differences that are likely attributable to alterations in the nature of the protein-phosphate backbone interactions in the complex.

Because Taq polymerase can use up to 3 different dNTP ($\alpha$S)s in the polymerization reaction, further backbone substitutions are possible. The present invention contemplates the incorporation of both triphosphate and triphosphate ($\alpha$S) nucleotides in the PCR mix so that a library of both phosphate and monothiophosphate backbones may be randomized at the same base position, greatly increasing the diversity of the library.

A. Library Generation

A random combinatorial library of normal phosphoryl backbone oligonucleotides was synthesized by automated DNA synthesis (Midland Certified Reagents, Midland, Tex.) programmed to include all 4 monomer bases of the oligonucleotide during the coupling of residues in a randomized segment. This synthetic library has PCR primer segments at the 5' and 3' ends flanking the randomized region and thus can be replicated and amplified by Taq DNA polymerase (AMPLITAQ, Perkin Elmer). A 66-mer has been used with a 22 base pair random central segment flanked by 21 and 23 base pair PCR primer regions:

5'CAGTGCTCTAGAGGATCCGTGAC $N_{22}$ CGAAGCTTATCGATCCGAGCG3'(SEQ ID NO.:1).

The resulting library thus exists as a population with potentially $4^{22}$ ($10^{13}$) different sequences. The oligonucleotide library with phosphorothioate backbone substituted at dA positions was then synthesized by PCR amplification of the 66-mer template using commercially available Taq polymerase and a mix of dATP($\alpha$S), dTTP, dGTP and dCTP as substrates (Pharmacia, Inc.). The PCR amplification of the starting random library included: 40 $\mu$M each of dATP($\alpha$S), dTTP, dGTP and dCTP, 500 $\mu$M $MgCl_2$, 2.9 $\mu$M 66mer random template, 5 U Taq polymerase and 400 nM each primer in a total volume of 100 $\mu$L. PCR was run for 25 cycles of 95° C./1 min, 72° C./1 min. This polymerase is known to PCR amplify a phosphorothioate backbone template (Nakamaye et al. *Nucl. Acids Res.* (1988) 16: 9947) so long as the dNTP($\alpha$S) 's are limited to no more than 3 different bases in the mixture (Ciafre et al. *Nucl. Acids Res.* (1995) 23:4134). It also acts stereospecifically to incorporate the $S_p$-diastereomers of dNTP($\alpha$S) 's and is believed to yield the $R_p$ stereoisomer as is found for other polymerases (Eckstein, F. *Ann. Rev. Biochem.* (1985) 54: 367).

B. NF-IL6 Preparation

When full length NF-IL6 complexed with DNA is exposed to trypsin, a 9.5 kDa fragment is identified as the smallest fragment stably resistant to proteolysis. This basic leucine zipper (bZIP) domain peptide spans amino acids $A^{266}$–$C^{345}$, and is termed the NF-IL6 tryptic core domain (TCD).

High level expression of recombinant NF-IL6 bZIP region in E. coli was achieved in the T7 promoter/polymerase system. The TCD expressed as a nonfusion protein constitutes 30% of the total soluble E. coli protein and was purified as previously described (Brasier, et al., J. Biol. Chem. (1994) 269: 1034). The TCD bZIP domain binds DNA in a manner indistinguishable from full length NF-IL6. Electrospray mass spectrometry indicates that the mass of TCD is 18,926 Da. These data indicated that TCD is a covalently linked dimer through its C-terminal disulfide bond. The present selection, however, was performed under conditions in which the disulfides are reduced and the TCD exists as a non-covalent dimer.

C. NF-IL6 Thiophosphate selection

The random library was screened to determine sequences that have affinity to the bZIP domain of NF-IL6. PCR amplification of the single stranded library provided chiral duplex phosphorothioate 66-mer at all dA positions (except for the primer segments). A filter-binding method was used for enrichment of binding sites, although other methods known in the art are also suitable. The PCR amplified random library of the chiral duplex phosphorothioate 66-mer at dA positions (100 pmols) was incubated with 6.6 pmols TCD in 50 µl buffer containing 10 mM Tris, pH 7.5, 1 mM DTT and 50 to 400 mM KCl and filtered through Millipore HAWP25 mm nitrocellulose filters (following a modification of the protocol from Thiesen et al., Nucl. Acids Res. (1990) 18: 3203). The filters had been previously presoaked in 1× binding buffer that contains no protein or DNA (10 mM Tris, pH 7.5, 1 mM DTT and 50 to 400 mM KCl). Under these conditions the DNA/protein complexes were retained on the filter. The filter was then washed with 10 ml of 1× binding buffer to remove the majority of the DNA that only weakly bound to the protein.

A 1 ml solution of 8 M urea and 4 M NaCl was then added to elute the protein-bound DNA. A negative control without protein was performed simultaneously to monitor any non-specific binding of the thiophosphate DNA library to the nitrocellulose filter. DNA was ethanol precipitated and once again PCR amplified with the dATP(αS) nucleotide mix. The PCR thermal profile was different than that used to make the starting library: 95° C./1 min, 55° C./1 min, 68° C./1 min for 25 cycles. The PCR products were analyzed by 15% non-denaturing polyacrylamide gel electrophoresis.

At various stages of the selection process the resulting libraries were cloned and plasmids from individual colonies sequenced. The normal phosphate ester 66-mer duplexes in the libraries were sub-cloned using the TA cloning kit (Invitrogen). As a control, four clones were also sequenced from the original combinatorial library and shown to have random sequence.

The present invention provides a thiophosphate backbone combinatorial library created by PCR methods with substitution of appropriate dNTP(αS) in the Taq polymerization step. This combinatorial thiophosphate duplex library was successfully screened for binding to the TCD of NF-IL6 by a filter binding method that was modified to minimize non-specific binding of the thiophosphate oligonucleotides to the nitrocellulose filter. The thiophosphate substituted DNA may be eluted from the filter using, e.g., high salt, protein denaturing conditions described or other conditions known in the art. Subsequent ethanol precipitation and another PCR thiophosphate amplification provide product pools for additional rounds of selection may also be used to further select for high affinity binding. In order to increase the stringency of binding of the remaining pool of DNA in the library (thereby, selecting tighter binding members of the library), the KCl concentration was increased in subsequent rounds from 50 to 400 mM. The stringency of selection was also manipulated by lowering the amount of protein as the iteration number increased.

The first selection was carried through 7 iterations. Only 3 clones were selected and sequenced (Table-1) at this stage of the selection process. In all 3 early round clones (3:3), a general consensus sequence was found with a stretch of 8–11 A/C's including the sequences: ACAACCC or ACAC-CACC. NF-IL6 is a CCAAT/enhancer-binding protein (C/EBPβ) with specificity for two CCAAC/T boxes. Thus in these early rounds of selection, the thiophosphate substitution at dA did not dramatically altered the affinity for the "CAAC"-like box.

A second independent selection included 10 iterations and yielding the sequences also shown in Table 1 (4 of 4 clones). As shown in Table 1, the two independent selection experiments identified a single unique sequence (compare clones #2 and #7). While the ACAACCC sequence once again appeared (#7), another unique new sequence (dGGGCCC GCTGT ACATG C ACACG, SEQ ID No.: 5, clones #4–6) was found for the entire 22-bp randomized segment. The Table has been divided to emphasize homology among 5–6 bp consensus, putative recognition units:

| "GC-box" | Duplex format |
|---|---|
| "5'ACAGC.GCTGT" | 5' ACAGC<br>TGTCG 5' |
| "5'ACATG.CATGT" | 5' ACATG<br>TGTAC 5' |
| "5'ACACG.CGTGT" | 5' ACACG<br>TGTGC 5' |

Nascent elements of this new variation were also observed at round 7 of the first selection(GC box, ACA and ACACG units).

TABLE I

Sequences of Variable 22-mer Region in 66-mer Thiophosphate Aptamers, Selected after Indicated Rounds.*

| CONSENSUS | GC-box | ACAGC.GCTGT | ACATG.CATGT | ACACG.CGTGT |
|---|---|---|---|---|
| 1st INDEPENDENT SELECTION STUDY, ROUND 7 | | | | |
| 1 (SEQ ID No.: 2) | 5'd GCC | GTCC | ACATA C G | ACACCACC |
| 2 (SEQ ID No.: 3) | 5'dGGCC | GACCGC | ACA G C | ACAACCC |
| 3 (SEQ ID No.: 4) | 5'dGGC | GCGGAT | ACAAC C C | ACACGC |

TABLE I-continued

Sequences of Variable 22-mer Region in 66-mer
Thiophosphate Aptamers, Selected after Indicated Rounds.*

| CONSENSUS | GC-box | ACAGC.GCTGT | ACATG.CATGT | ACACG.CGTGT |
|---|---|---|---|---|
| 2nd INDEPENDENT SELECTION STUDY, ROUND 10 | | | | |
| 4 (SEQ ID No.: 5) | 5'dGGGCCC | GCTGT | ACATG C | ACACG |
| 5 (SEQ ID No.: 5) | 5'dGGGCCC | GCTGT | ACATG C | ACACG |
| 6 (SEQ ID No.: 5) | 5'dGGGCCC | GCTGT | ACATG C | ACACG |
| 7 (SEQ ID No.: 6) | 5'dGGCC | GACCGC | ACA G C | ACAACCC |
| ROUND 16: Family A | | | | |
| 8 (SEQ ID No.: 7) | 5'GGGCCC | GCTGT | ACATG C | ACACG |
| 9 (SEQ ID No.: 7) | 5'GGGCCC | GCTGT | ACATG C | ACACG |
| 10 (SEQ ID No.: 7) | 5'GGGCCC | GCTGT | ACATG C | ACACG |
| 11 (SEQ ID No.: 7) | 5'GGGCCC | GCTGC | ACGTG C | ACACG |
| 12 (SEQ ID No.: 8) | 5'GGGCCC | GCTGT | ACACG C | ACACG |
| ROUND 16: Family B | | | | |
| 13 (SEQ ID No.: 9) | 5' CCC | GTTGT | TGTCCCACT | CCACG |
| 14 (SEQ ID No.: 10) | 5' CCC | GTTGT | TGTCCCGCT | CCACG |

*Sequences are aligned to highlight the consensus elements (underlined). All sequences are written such that the first six flanking 5' and 3' primer sequences are all 5'GCTTCG and 5'CTCACC, respectively.

The 10th pool of the second selection was carried through additional 6 iterations and in the 7 clones sequenced, two major sequence families were obtained (Table 1): Family A) typified by 5'dGGGCCC GCTGT ACATG C ACACG (SEQ ID No.: 7) and Family B) typified by 5'dCCC GTTGT TGTCCCACT CCACG (SEQ ID No.: 9). Within these 22-base sequences only 1 or 2 base changes were found for each family (3 of the 7 were identical sequences; clones #8–10). Note that even by round 10, three members of the 22-base sequence are identical to the A family consensus sequence (clones #4–6). Family B retains the early round CAAC.GTTG consensus while family A has lost all "traditional" C/EBPβ CAAC/T box sequence homology. An additional group of 25 clones were sequenced (data not shown) and the 22-mers were found to also fall within the two families (identical to the consensus sequence or differing by only 1 nucleotide).

These results differ from normal phosphate ester backbone in vitro selection studies with NF-IL6, where a traditional CAAC box was identified using the same TCD of NF-IL6 and 66-mer library under identical selection conditions. Osada, et al. (*J. Biol. Chem.* (1996) 271:3891), used full-length C/EBPβ and a 16 nucleotide randomized library to determine a 10-bp consensus sequence showing the expected two half-site GTTGC.GCAAC in a palindromic sequence as shown in Table 2.

TABLE 2

Comparison of Putative Phosphodiester and
Thiophosphate Consensus Recognition Sequences

| Consensus phosphate ester (Osaka) | GTTGC GCAAC | (SEQ ID No.: 11) |
|---|---|---|
| Consensus thiophosphate ester(Family A) | GCTGT ACATG | (SEQ ID No.: 12) |
| Consensus thiophosphate ester(Family B) | GTTGT CCCAC or GTTGT TGTCC* | (SEQ ID No.: 13) (SEQ ID No.: 14) |

*(alignment of a consensus sequence is more difficult for Family B members)

Thiophosphate substitution of dA altered the sequence selected, thereby eliminating the sequential AA consensus sequence (Family A only) found in all other phosphate selection studies.

In both normal phosphate and thiophosphate duplex 10-mers, 4–5 dA's may be found, indicating that thiophosphate substitution for the dA residues has not had a deleterious effect on binding.

D. Affinity Measurements by Fluorescence Polarization The affinity of the selected oligo's or libraries have been measured by fluorescence anisotropy (Heyduk et al. *Proc. Natl. Acad. Sci., U.S.A.* (1990) 87: 1744). Fluorescence polarization titrations using increasing concentrations of the recombinant protein to bind a palindromic 5'-labeled fluorescein C/EBPβ 20-mer binding site with a normal phosphate ester backbone (dTGCAGATTGCGCAATCTGCA: SEQ ID No.: 15) gave an observed binding constant, $K_{obs}$, of 10 nM.

Thiophosphate 66-mers were PCR amplified, phenol extracted and ethanol precipitated. DNA purity was >95% as assessed by PAGE gels. Varying concentrations of 66-mers, 5'-Labeled fluorescein-20-mer palindromic binding site and NF-IL6 TCD dimer were incubated in 10 mM Tris, pH 7.5, 50 mM KCl, 1.0 mM DTT buffer for 1 hour prior to fluorescence polarization measurements. Concentrations of 66-mer were calculated at 20 $OD_{260}$/mg. The observed binding constant, $K_{obs}$, represented the 66-mer concentration providing a 50% decrease in the fluorescence polarization intensity change. Fluorescence polarization titrations were carried out on a Panvera Beacon polarimeter.

Figure 1:
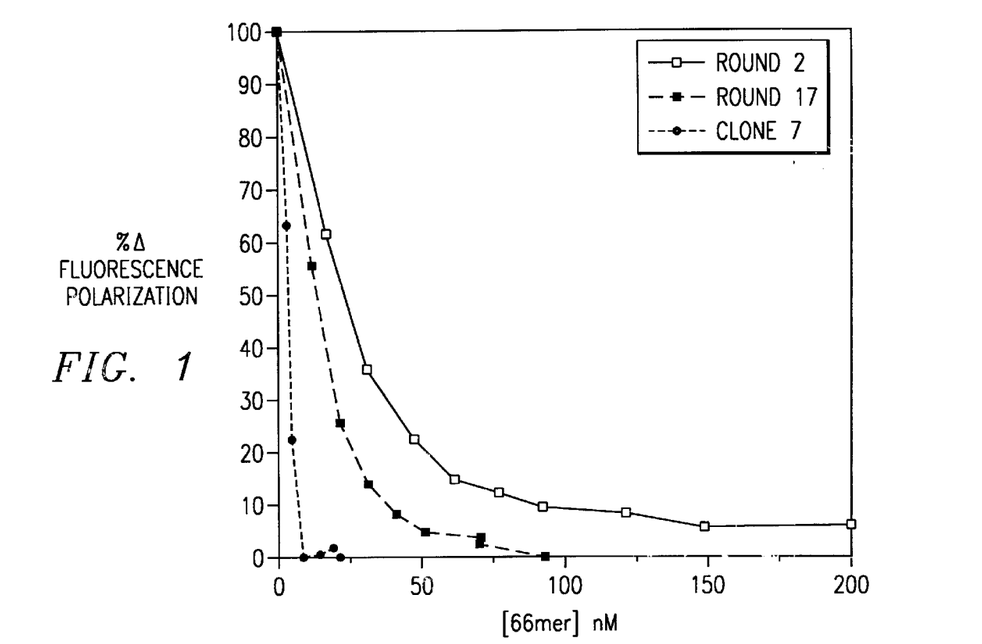
FIG. 1 depicts a competitive fluorescence polarization titration of 5'-labeled fluorescein-20-mer duplex/NF-IL6 TCD dimer complex.

The monothiophosphate libraries and individual 66-mer sequences were used as competitors to dissociate a fluoroscein-labeled, normal backbone duplex C/EBPβ 20-mer bound to the bZIP protein. As shown in FIG. 1, an individual monothiophosphate 66-mer cloned from the 10th selection round (clone #7) gave a $K_{obs}$ of <2 nM.

Figure 2:
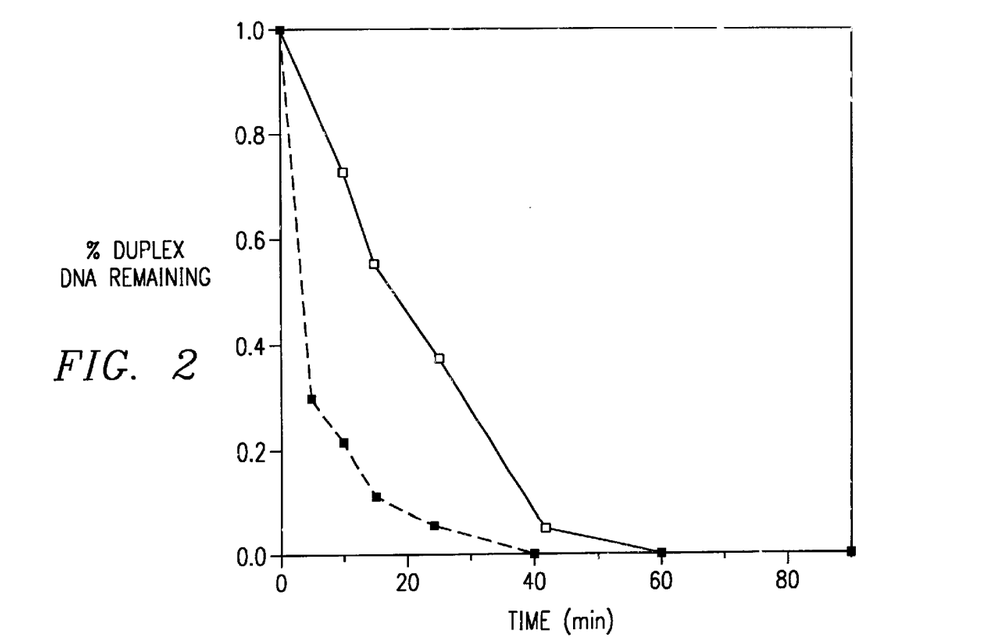
FIG. 2 depicts relative sensitivity of Family A 66-mers to degradation by DNase I. Unmodified, phosphoryl duplex (●) and monothiophosphorylated at non-primer dA sites only (□).

FIG. 2 depicts relative sensitivity of Family A 66-mers to degradation by DNase I. Unmodified, phosphoryl duplex (●) and monothiophosphorylated at non-primer dA sites only (□).

Figure 3A:
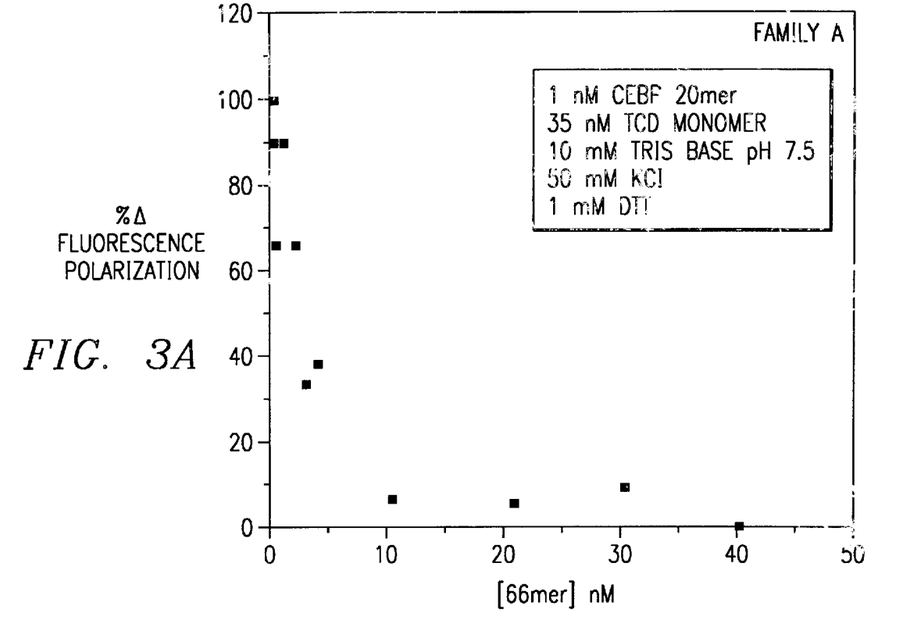
FIG. 3 is a negative control, at a concentration of up to 4 $\mu$m, thiophosphate clone 98 (Family A) was shown not to bind to another transcription factor, NF-kB (p65 dimer).
Figure 3B:
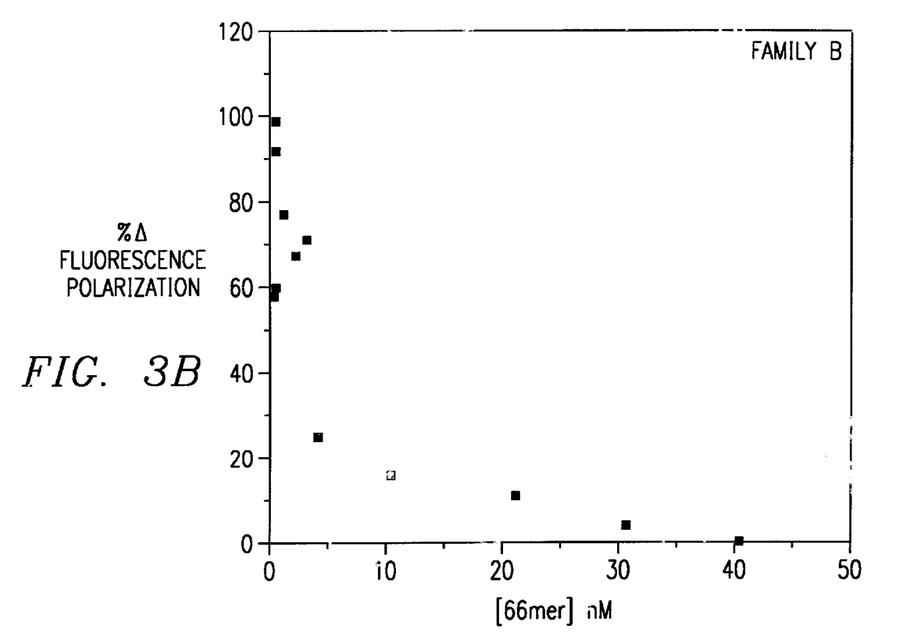

Following a similar competitive titration, monothiophosphate (at dA) clones #8 and 13 (consensus Family A and B, respectively) also gave a Kb of <2 nM (FIG. 3). As a negative control (data not shown), at a concentration of up to 4 μM, thiophosphate clone #8 (Family A) was shown not to bind to another transcription factor, NF-kB (p65 dimer).

Figure 4A:
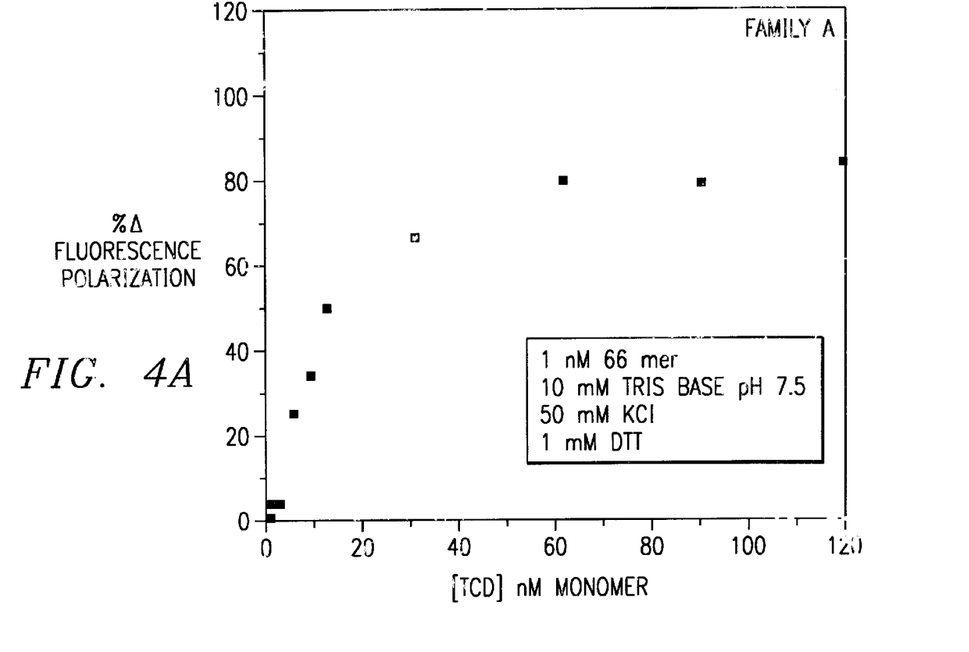
FIG. 4 depicts these titrations performed directly whereby each aptamer was fluorescein labeled and the protein was titrated into the solution. These assays gave similar estimates of the binding constants (Family A 5 nM and Family B 3 nM, monomer concentration giving 50% saturation).
Figure 4B:
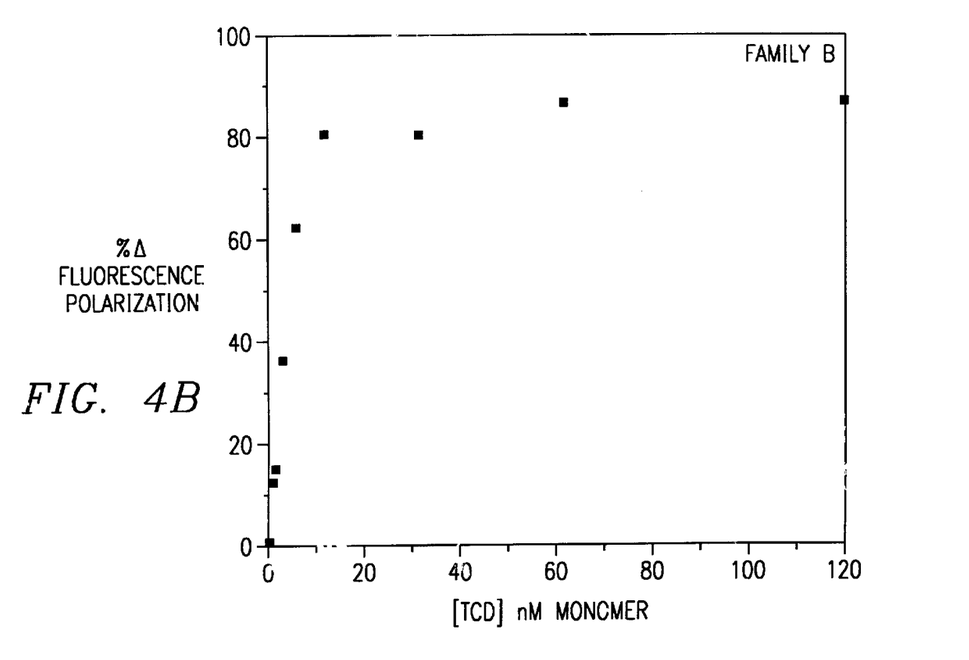

These titrations were also performed directly where each aptamer was fluorescein labeled and the protein was titrated into the solution. These assays gave similar estimates of the binding constants (Family A 5 nM and Family B 3 nM, monomer concentration giving 50% saturation, FIG. 4).

Stoichiometric titration of 66-mers with TCD established that later rounds (FIG. 1) bound the protein dimer with an approximate 2:1 (protein dimer: DNA duplex) stoichiometry. Initial rounds bound to TCD with a 1:1 stoichiometry (FIG. 1). This change in stoichiometry may explain the remarkable selection of a full 22-base sequence when the NF-IL6 consensus site is believed to be only 10 bases in length.

The crystal structure of leucine zipper proteins such as GCN4 and AP-1 in the DNA cocrystal are coiled coils (Ellenberger et al. *Cell* (1992) 71: 1223), with the basic region coiling into a helix to bind in the major groove in each of the half sites. In a bZIP protein such as NF-IL6, it would be expected that each basic region of the protein binds as an alpha-helix to the two CAAC/T half-sites in the generally palindromic recognition sequences.

In order to explain the 2:1 stoichiometry for binding Family A consensus 22-mer sequence, two TCD dimers must be capable of orienting on the duplex. Note that the Family A 22-mer contains the consensus sequence:

5' dGGGCC C GCTGT ACATG C ACACG (SEQ ID No.: 7) CCCGG G CGACA TGTAC G TGTGCd 5' (SEQ ID No.: 16).

There are three very similar sequences shown above in bold: 5'ACAGC, 5' ACATG, 5'ACACG, which were being selected even in rounds 7–10, and remarkably, in the same orientation and order shown above (Table 1). This degree of conservation suggests that one TCD dimer can bind with each basic recognition helix interacting with each of the 5 nucleotide sequences (containing ACA.TGT triplets) shown in bold. The second TCD dimer may bind to one of the two basic recognition helices recognizing the 3rd 5 nucleotide sequence in bold.

The six N-terminal residues of TCD are required for binding to the NF-IL6 consensus sequence (Brasier et al. *J. Biol. Chem.* (1994) 269: 1034). Although not part of the basic domain of the protein, NMR structural studies by the present inventors show that there is considerable helical content in this region. E. Nuclease resistance of thioated aptamers The sensitivity of the duplexes to DNase I degradation was monitored by native PAGE. Reaction mixtures contained either 40.5 or 33.8 $\mu$g/ml duplex (phosphoryl or thiophosphoryl, respectively) in 205 $\mu$L of 50 mM Tris, 10 mM $MgCl_2$, 50 $\mu$g/mL BSA, pH 7.5 buffer and 0.12 pg/mL DNase I (Sigma). Aliquots (20 $\mu$l) were removed at specific time points and the hydrolysis quenched by adding 4 $\mu$l 0.5 M EDTA, 20 $\mu$l 90% formamide, followed by boiling and storing at 0° C. Gels were scanned and the 66-mer lane integrated using an Image ID gel scanner (Pharmacia).

As shown in FIG. 2, thiophosphorylation of the Family A 66-mer at only the dA sites (excepting the primers) results in a duplex that is more resistant to DNase I degradation than the unmodified 66-mer. Increased nuclease resistance was generally found for both endonucleases such as DNase I or exonucleases such as Bal 31.

While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

What is claimed is:

1. A method of identifying an aptamer comprising the steps of:
   (a) synthesizing a random phosphodiester oligonucleotide combinatorial library wherein constituent oligonucleotides comprise at least a set of 5' and 3' PCR primer nucleotide sequences flanking a randomized nucleotide sequence;
   (b) amplifying the library enzymatically using a mix of four nucleotides, wherein one or more of the nucleotides comprises a mix of unmodified and thiophosphate-modified nucleotides, to form a partially thiophosphate-modified oligonucleotide combinatorial library;
   (c) contacting the partially thiophosphate-modified oligonucleotide combinatorial library with a target molecule and isolating a subset of oligonucleotides binding to the target molecule;
   (d) amplifying the subset of binding oligonucleotides enzymatically using a mix of four nucleotides, wherein at least a portion of at least one nucleotide is thiophosphate-modified, to form a thiophosphate-modified oligonucleotide sub-library; and
   (e) repeating steps (c)–(d) iteratively with increased stringency of the contacting step between each iteration until at least one aptamer comprising a thiophosphate-modified oligonucleotide population of defined sequence is obtained.

2. The method of claim 1, wherein the modified nucleotide comprises a phosphorothioate.

3. The method of claim 1, wherein the modified nucleotide comprises a phosphorodithioate.

4. The method of claim 1, wherein the modified nucleotide is selected from the group consisting of dATP($\alpha$S), dTTP($\alpha$S), dCTP($\alpha$S) and dGTP($\alpha$S).

5. The method of claim 1, wherein no more than three adjacent phosphate sites are replaced with phosphorothioate groups.

6. The method of claim 1, wherein at least a portion of non-adjacent phosphate sites are replaced with phosphorothioate groups.

7. The method of claim 1, wherein no more than three adjacent phosphate sites are replaced with phosphorodithioate groups.

8. The method of claim 1, wherein at least a portion of non-adjacent phosphate sites are replaced with phosphorodithioate groups.

9. The method of claim 1, wherein the target is a nucleic acid binding protein.

10. The method of claim 1, wherein the target is NF-IL6.

11. A method of identifying a set of aptamers containing an optimal composition of thiophosphate-modified nucleotides such that the aptamers bind with high affinity to a target molecule, and have increased resistance to nuclease degradation, said method comprising the steps of:
    (a) synthesizing a random partially thiophosphate-modified oligonucleotide combinatorial library wherein at least a portion of the oligonucleotide phosphate groups are thiophosphate-modified nucleotides, and where no more than three of the four different nucleotides are substituted on the 5'-phosphate positions by 5'-thiophosphates in each synthesized oligonucleotide are thiophosphate-modified nucleotides;
    (b) amplifying the library enzymatically using a mix of four nucleotides, wherein one or more of the nucleotides comprises a mix of unmodified and thiophosphate-modified nucleotides, whereby no more than three adjacent phosphate sites in each amplified oligonucleotide are thiophosphate-modified nucleotides;
    (c) contacting the amplified library with a target molecule under conditions favorable for binding of a binding oligonucleotide with said target molecule;
    (d) isolating a subset of binding oligonucleotides from the library, that bind with higher affinity to the target molecule relative to the original amplified library; and
    (e) amplifying the subset of binding oligonucleotides enzymatically using a mix of four nucleotides, wherein one or more of the nucleotides comprises a mix of unmodified and thiophosphate-modified nucleotides.

12. The method of claim 11, further comprising the step of:
    (f) repeating steps (c)–(e) iteratively, whereby an enriched subset of oligonucleotides binding with higher affinity to the target molecule relative to the original amplified subset, is isolated after each cycle.

13. The method of claim 12, whereby each iteration is performed under conditions of increased stringency in the contacting step until a subset of high affinity binding oligonucleotides is identified.

14. The method of claim 11, whereby synthesis of the combinatorial library is done using constituent oligonucleotides comprising at least a set of 5' and 3' PCR primer nucleotide sequences flanking a randomized nucleotide sequence.

15. The method of claim 11, whereby the subset of amplified oligonucleotides is cloned and where individual thiophosphate-modified oligonucleotides that bind to the target are isolated and sequenced.

16. The method of claim 15, whereby the isolated aptamer is screened relative to its respective non-modified oligonucleotide, to possess:
    (a) increased affinity for the target, and
    (b) increased stability with respect to nuclease degradation.

17. The method of claim 16, whereby the thiophosphate comprises a phosphorodithioate.

18. The method of claim 16, whereby the thiophosphate comprises a phosphorothioate or phosphorodithioate.

19. A method of identifying an aptamer that specifically recognizes NF-IL6, comprising the steps of:
    (a) synthesizing a random phosphodiester oligonucleotide combinatorial library wherein constituent oligonucleotides comprise at least a set of 5' and 3' PCR primer nucleotide sequences flanking a randomized nucleotide sequence;
    (b) amplifying the library enzymatically using a mix of four nucleotides, wherein one or more of the nucleotides comprises a mix of unmodified and triphosphate (alpha-S) modified nucleotides to form a thiophosphate-modified oligonucleotide combinatorial library;
    (c) contacting the thiophosphate-modified oligonucleotide combinatorial library with an NF-IL6 target molecule and isolating a subset of oligonucleotides binding to the NF-IL6 target molecule;
    (d) amplifying the subset of binding oligonucleotides enzymatically using a mix of four nucleotide nucleotides, wherein a portion of at least one and no more than three of the nucleotide nucleotides in the mix is a nucleotide triphosphate, to form a thiophosphate-modified oligonucleotide sub-library; and (e) repeating steps contacting and amplifying the oligonucleotides iteratively with increased stringency of the contacting step between each iteration until at least one aptamer comprising a thiophosphate-modified oligonucleotide population of defined sequence and site of thiophosphate substitution is obtained and only a portion of the oligonucleotide is substituted.

20. The method of claim 19, whereby the thiophosphate comprises a phosphorodithioate.

21. The method of claim 19, whereby the thiophosphate comprises a phosphorothioate and phosphorodithioate.

* * * * *

SEQUENCE LISTING

<160> NUMBER OF SEQ ID NOS: 15

<210> SEQ ID NO 1
<211> LENGTH: 66
<212> TYPE: DNA
<213> ORGANISM: Artificial Sequence
<220> FEATURE:
<221> NAME/KEY: unsure
<222> LOCATION: (23)..(45)
<223> OTHER INFORMATION: n's = A, T, G, C or corresponding chemically
      modified nucleotides
<223> OTHER INFORMATION: Description of Artificial Sequence: random
      chemically synthesized combinatorial library
      having PCR primer sequences flanking a randomized
      region

<400> SEQUENCE: 1
cagtgctcta gaggatccgt gacnnnnnnn nnnnnnnnnn nnnncgaag cttatcgatc      60 cgagcg                                                                66

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: aptamer

<400> SEQUENCE: 2

```
gccgtccaca tacgacacca cc                                              22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: aptamer

<400> SEQUENCE: 3
ggccgaccgc acagcacaac cc                                              22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: aptamer

<400> SEQUENCE: 4
ggcgcggata caacccacac gc                                              22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: aptamer

<400> SEQUENCE: 5
gggcccgctg tacatgcaca cg                                              22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: aptamer

<400> SEQUENCE: 6
ggccgaccgc acagcacaac cc                                              22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: aptamer

<400> SEQUENCE: 7
gggcccgctg tacatgcaca cg                                              22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: aptamer

<400> SEQUENCE: 8
gggcccgctg tacacgcaca cg                                              22

<210> SEQ ID NO 9
<211> LENGTH: 22
<212> TYPE: DNA
<213> ORGANISM: Artificial Sequence
```

```
<220> FEATURE:
<223> OTHER INFORMATION: Description of Artificial Sequence: aptamer

<400> SEQUENCE: 9
cccgttgttg tcccactcca cg                                              22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: aptamer

<400> SEQUENCE: 10
cccgttgttg tcccgctcca cg                                              22

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: aptamer

<400> SEQUENCE: 11
gttgcgcaac                                                            10

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: aptamer

<400> SEQUENCE: 12
gctgtacatg                                                            10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: aptamer

<400> SEQUENCE: 13
gttgtcccac                                                            10

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: aptamer

<400> SEQUENCE: 14
gttgttgtcc                                                            10

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: aptamer

<400> SEQUENCE: 15
tgcagattgc gcaatctgca                                                 20
```